Nov. 10, 1953 R. L. BYRUM Plant Pat. 1,227
ROSE PLANT
Filed Oct. 20, 1952
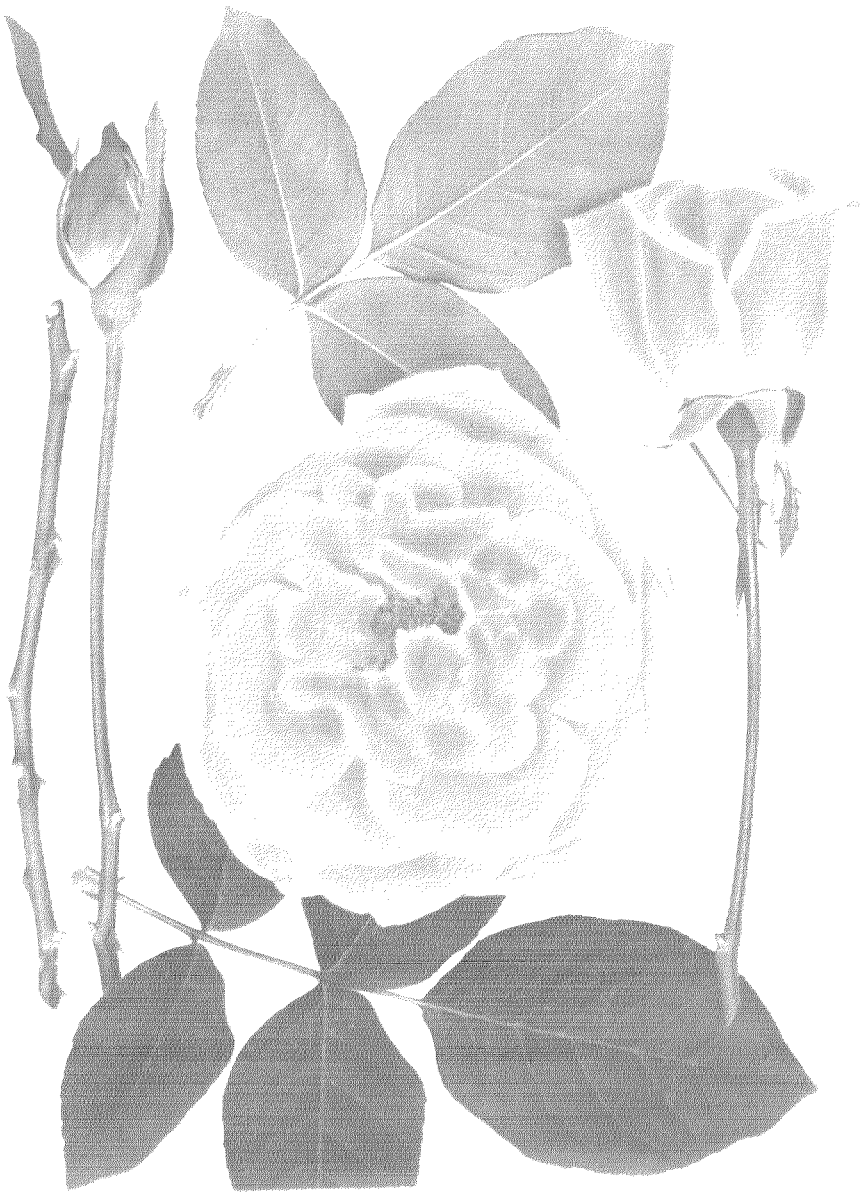
Inventor
R. L. Byrum
By: Robb & Robb
Attorneys Patented Nov. 10, 1953

Plant Pat. 1,227

UNITED STATES PATENT OFFICE 1,227

ROSE PLANT

Roy L. Byrum, Richmond, Ind., assignor to Joseph H. Hill Company, Richmond, Ind., a corporation of Indiana Application October 20, 1952, Serial No. 315,856

1 Claim. (Cl. 47—61)

The present invention relates to a new and distinct variety of rose plant of the hybrid tea class, originated by me by crossing the variety "Pink Bountiful" (Plant Patent No. 601) with the variety "Celebrity" (Plant Patent No. 695).

The primary objective in making this cross was to produce a new variety of rose comparable to the variety known as "Celebrity," but with the improvement of more abundant production of blooms per plant, and having flowers which open better in mid-winter. This objective was fully achieved, as evidenced by the fact that my new variety is altogether different in color and type from its seed parent "Pink Bountiful," produces more blooms per plant and has longer buds than its pollen parent "Celebrity," and the flowers of the new variety open well under greenhouse conditions in mid-winter, and do not tend to grow "bull-headed." In addition to these novel features which clearly distinguish the new variety from its parents, as well as from all other varieties of its class, my new variety is further characterized as to novelty by the distinctive and strong tea fragrance of its blooms, and by the distinctive color of its blooms, varying in general color tonality from Neyron Rose in the newly open flowers, to Rose Madder in the 3-days open flowers.

Asexual reproduction of my new variety by both grafting and budding, as performed at Richmond, Indiana, shows that the foregoing characteristics and distinctions come true to form and are established and transmitted through succeeding propagations.

The accompanying drawing shows specimens of the flowers, foliage and stems of my new variety, with the flowers depicted in different stages of development from the bud stage to the fully-open bloom.

The following is a detailed description of my new variety, with color terminology in accordance with Ridgway's Color Standards and Nomenclature (hereinafter abbreviated as "Ridgway"), or Robert F. Wilson's Horticultural Colour Chart (hereinafter abbreviated as "Wilson") or Koster's Color Guide (hereinafter abbreviated as "Koster"), as indicated:

Type: Bush; for greenhouse plantings.
Class: Hybrid tea.
Parentage: Seedling.
*Seed parent.*—"Pink Bountiful."
*Pollen parent.*—"Celebrity."
Propagation: Holds its distinguishing characteristics through succeeding propagations by grafting and by budding.
Locality where grown and observed: Richmond, Indiana.

*Flower*

Flowers borne: Singly to stem; on medium-strong, medium-length stems.
Quantity of bloom: Abundant.
Continuity: Continuous.
Fragrance: Penetrating; tea.
Bud:
*Peduncle.*—Medium-length; medium-diameter; erect. Bark—smooth. Color—Scheele's Green, Plate 860 (Wilson). Thorns—none. Prickles—numerous. Color—Pea Green, Plate 61/3 (Wilson). Hairs—few. Color—Pea Green, Plate 61/3 (Wilson).
*Before calyx breaks.*—Size—medium-small. Form—short; pointed; with a conspicuous neck; without foliaceous appendages on the surface of the bud; with slender foliaceous parts extending beyond the tip of the bud equal to ¾ or more of its length. Color—Scheele's Green, Plate 860 (Wilson).
*As calyx breaks.*—Color (outside of petal)—Rose opal, Plate 022/1 (Wilson).
*As first petal opens.*—Size—medium-large. Form—long; pointed. Color—outside: Carmine, Plate 29 (Koster), changing to Cream Yellow, Plate 4 (Koster) at base; inside: Begonia, Plate 619 (Wilson), changing to Chrome Yellow, Plate 605/1 (Wilson) at base. Opening—opens up well; no unusual characteristics result from effects of hot weather.
Bloom:
*Size (when fully open).*—Medium-large; from 3½ inches to 4½ inches.
*Petalage.*—Double; from 28 to 30 petals arranged irregularly.
*Form.*—High-centered at first; becoming open; petals being at first tightly rolled outward; becoming later at maturity loosely rolled outward.
*Petals.*—Moderately thick; soft. Inside surface—satiny; outside surface—satiny. Shape—outside petals—obovate; apex flat. Intermediate petals—obovate; apex flat; few with one notch. Inside petals—scalloped; obovate; apex retuse; with one notch.

This description of a newly open flower was made from a rose grown in a greenhouse in the month of June at Richmond, Indiana:

*Color of petals.*—Outside petal—outside surface: Neyron Rose, Plate 623/2 (Wilson), with Lemon Yellow, Plate 4/2 (Wilson) at base; inside surface: Neyron Rose, Plate 623/2 (Wilson), with Lemon Yellow, Plate 4/2 (Wilson) at base. Intermediate petal—outside surface: Spinel Pink, Plate 0625/2 (Wilson), with Lemon Yellow, Plate 4/2 (Wilson) at base; inside surface: Spinel Pink, Plate 0625/2 (Wilson), with Lemon Yellow, Plate 4/2 (Wilson) at base. Inner petal—outside surface: Spinel Pink, Plate 0625/2 (Wilson); few with Lemon Yellow, Plate 4/2 (Wilson) streak running up center; inside surface: Spinel Pink, Plate 0625/2 (Wilson); few with Lemon Yellow, Plate 4/2 (Wilson) streak running up center.

This description was made from a rose that was open for three days in a greenhouse in the month of June at Richmond, Indiana:

*Color of petals.*—Outside petal—outside surface: Rose Madder, Plate 23/3 (Wilson), with Lemon Yellow, Plate 4/2 (Wilson) at base; inside surface: Phlox Pink, Plate 625/3 (Wilson), with Lemon Yellow, Plate 4/2 (Wilson) at base. Intermediate petal—outside surface: Rose Madder, Plate 23/3 (Wilson), with Lemon Yellow, Plate 4/2 (Wilson) at base; inside surface: Phlox Pink, Plate 625/3 (Wilson), with Lemon Yellow, Plate 4/2 (Wilson) at base. Inner petal—outside surface: Rose Madder, Plate 23/3 (Wilson); inside surface: Phlox Pink, Plate 625/3 (Wilson).

*Behavior of petals.*—Persist; normal behavior in hot weather, but fade to Rhodamine Pink, Plate 527/3 (Wilson).

*Flower longevity.*—Cut roses grown in greenhouse and kept at living room temperatures—4 days in May.

*General color effect of open bloom.*—Newly open flower—Neyron Rose, Plate 623/2 (Wilson). 3-days open—Rose Madder, Plate 23/3 (Wilson).

*Plant*

Foliage:

*Leaves.*—Compound of five leaflets; abundant; large size; heavy; leathery.

*Leaflets.*—Shape—ovoid. Apex—mucronate. Base—round. Margin—simply serrate. Color — mature — upper surface: Near Spinach Green, Plate 0960 (Wilson); under surface: Spinach Green, Plate 0960/2 (Wilson). Young—upper surface: Mineral Red, Plate XXVII (Ridgway); under surface: Mineral Red, Plate XXVII (Ridgway).

*Rachis (the supporting stem of the compound leaf).* — Heavy. Upper side — grooved; hairy. Under side—Rounded, not grooved; prickly.

*Stipules.*—Medium-length; narrow; with short points mostly turning out at an angle of more than 45°.

Growth:

*Habit.*—Bush; upright; much-branched.

*Growth.*—Vigorous.

*Canes.*—Medium diameter.

*Main stems.*—Color—Spinach Green, Plate 75 (Koster), overlaid with Maroon, Plate 97 (Koster). Thorns—several; medium-length; hooked downward; with short, narrow base. Color—Van Dyck Brown, Plate 96 (Koster). Prickles—none. Hairs—none.

*Branches.* — Color — Spinach Green, Plate 0960 (Wilson). Thorns—several; medium-length; hooked downward; with short, narrow base. Color—Oxblood Red, Plate 00823/3 (Wilson). Prickles — none. Hairs—none.

*New shoots.* — Color — Fern Green, Plate 0862/3 (Wilson). Thorns—several; medium-length; some straight and some hooked downward; with short, narrow base. Color—Spinel Red, Plate 0023/1 (Wilson). Prickles—none. Hairs—none.

*Reproductive organs*

Stamens: Many; arranged irregularly about pistils.

Filaments: Long; most with anthers. Color—Cadmium Orange, Plate 8/2 (Wilson).

Anthers: Medium; all open at once. Color—near Spanish Orange, Plate 010/1 (Wilson).

Pollen: Abundant. Color—Cadmium Orange, Plate 8/2 (Wilson).

Pistils: Many.

Styles: Uneven; short; thin; bunched. Color—Coral Pink, Plate 0619/1 (Wilson).

Stigma: Color—white.

Sepals: Permanent; medium-length; spear-shaped. Color—inside: Apple Green, Plate 77 (Koster); outside: near Spinach Green, Plate 960 (Wilson).

Hips: None.

Seeds: None.

I claim:

A new and distinct variety of rose plant of the hybrid tea class, substantially as herein shown and described, characterized particularly as to novelty by its improved and more abundant production of blooms per plant, by the longer bud form of its blooms, by the distinctive color of its open blooms varying in general color tonality from Neyron Rose in the newly open flower to Rose Madder in the 3-days open flower, by the distinctive and strong tea fragrance of its open flowers, and by the improved mid-winter opening habits of its flowers and the absence of "bull-heading" thereof in mid-winter.

ROY L. BYRUM.

No references cited.